United States Patent [19]

Hickey

[11] 4,144,893
[45] Mar. 20, 1979

[54] NEUROMUSCULAR THERAPY DEVICE

[75] Inventor: William Hickey, Short Beach, Conn.

[73] Assignee: Batrow Laboratories, Inc., Short Beach, Conn.

[21] Appl. No.: 844,983

[22] Filed: Oct. 25, 1977

Related U.S. Application Data

[63] Continuation of Ser. No. 725,520, Sep. 22, 1976, abandoned.

[51] Int. Cl.² .............................................. A61N 1/32
[52] U.S. Cl. ................................. 128/423 R; 128/405; 128/416; 313/201; 313/212; 339/118 R; 361/326
[58] Field of Search ............... 128/419 R, 420 R, 421, 128/422, 423 R, 404, 405, 410, 411, 413–418, 303.13, 303.14, 303.17, 303.18; 313/201, 166, 234, 312; 339/118 R, 118 RY; 361/326

[56] References Cited

U.S. PATENT DOCUMENTS

| 835,082 | 11/1906 | Schmidt | 128/417 X |
|---|---|---|---|
| 1,603,339 | 10/1926 | Herrmann | 128/415 |
| 1,805,904 | 5/1931 | Carpenter | 128/414 X |
| 2,104,252 | 1/1938 | Curtis | 128/405 |
| 2,216,269 | 10/1940 | Holmes | 313/201 X |
| 2,552,678 | 5/1951 | Hirbec | 313/201 |
| 2,617,421 | 11/1952 | Strong | 128/416 |
| 2,641,259 | 6/1953 | Batrow | 128/423 |
| 2,764,683 | 9/1956 | Paust et al. | 128/423 X |
| 2,772,679 | 12/1956 | Grabbert | 128/421 |
| 3,077,884 | 2/1963 | Batrow et al. | 128/423 |

FOREIGN PATENT DOCUMENTS

| 236579 | 3/1964 | Austria | 128/303.13 |
|---|---|---|---|
| 590745 | 6/1925 | France | 128/414 |

Primary Examiner—Lee S. Cohen
Attorney, Agent, or Firm—Hopgood, Calimafde, Kalil, Blaustein & Lieberman

[57] ABSTRACT

The invention contemplates an electroneuromuscular stimulator or therapy device wherein muscles may be stimulated through application of sufficiently characterized electrical pulses to a living body, via nerve endings related to the desired muscles to be stimulated. In the form disclosed, the device has proved to be of particular utility in equine electrotherapy. The device provides all power-source high-voltage generation and more delicate components in a single portable case, requiring only the attachment of flexible leads to a body-applicator electrode and to a body-grounding or return electrode; both body electrodes are rugged and are readily and safety applied by relatively unskilled personnel, subject to supervision or order of such licensed veterinary or other appropriate authority as local law may require.

14 Claims, 10 Drawing Figures

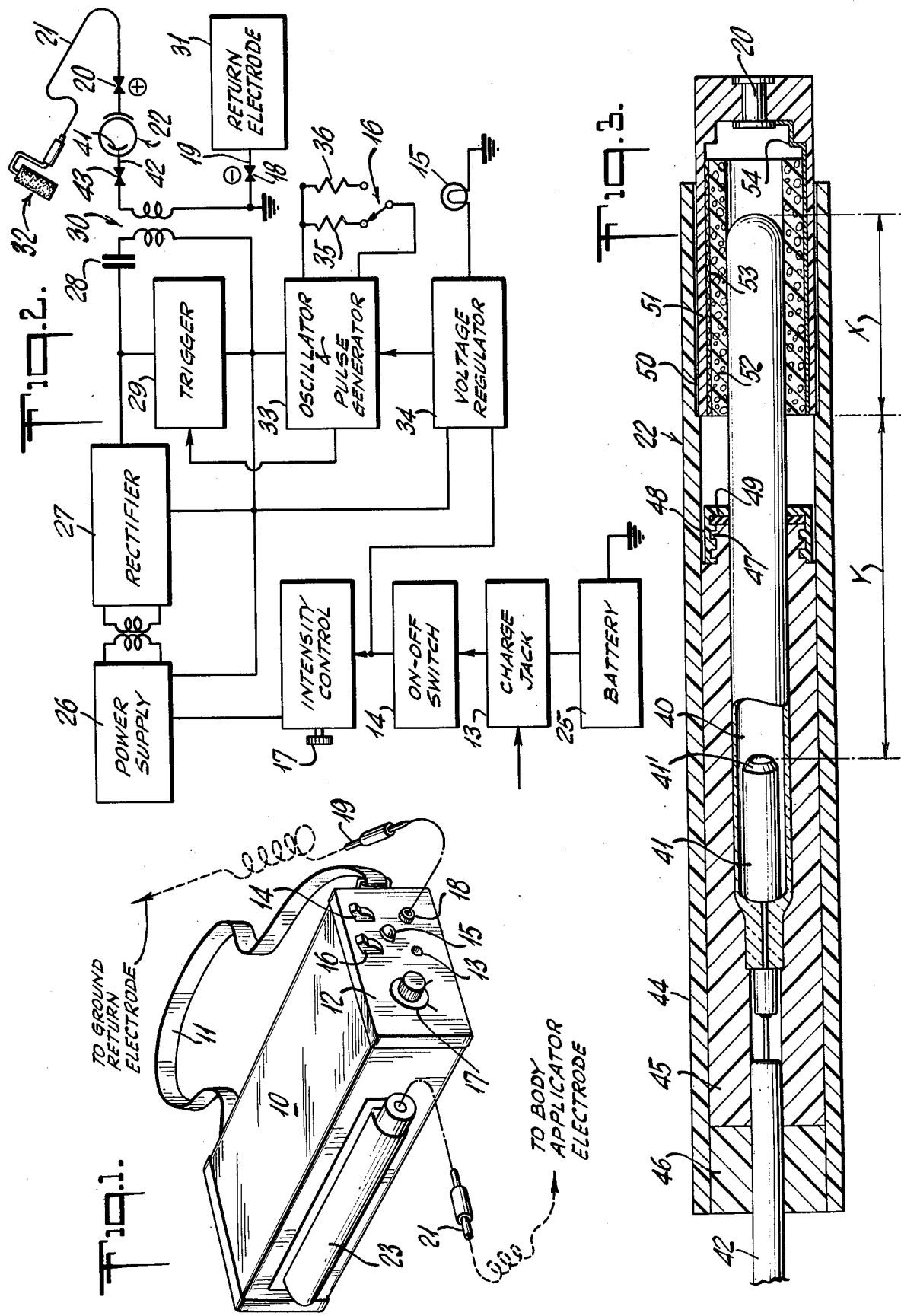

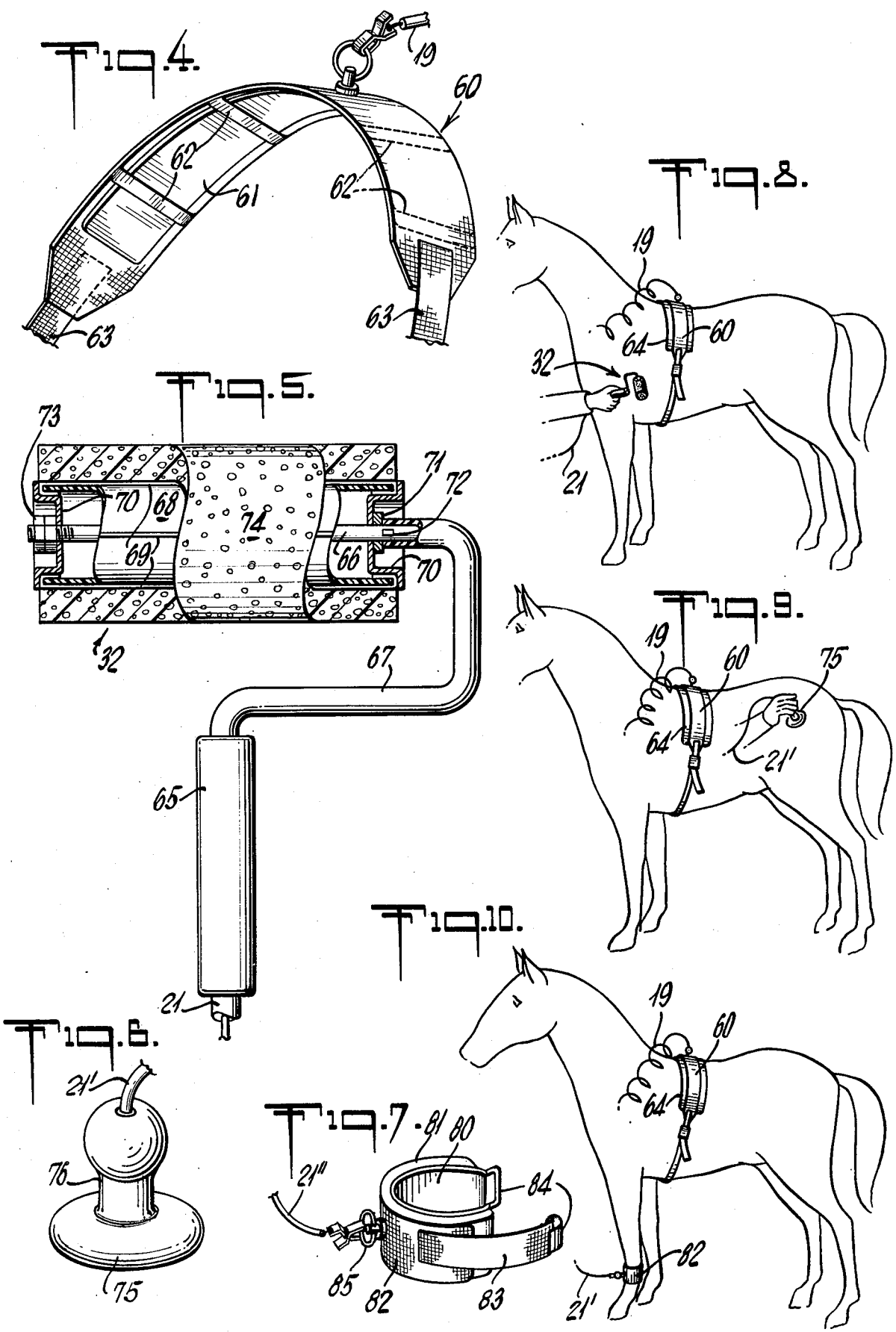

NEUROMUSCULAR THERAPY DEVICE

This is a continuation of copending application Ser. No. 725,520, filed Sept. 22, 1976, now abandoned.

This invention relates to electro-physiotherapy, and is particularly concerned with devices for neuromuscular stimulation, being of the general character disclosed in Batrow U.S. Letters Pat. No. 2,641,259 and No. 3,077,884.

When an animal cannot or will not sufficiently use its muscles in an injured area, for example, the area of a sprain, a strain, a bruise or a muscular cramp, then the proper flow of blood to the injured area is impaired. The flow of blood is needed to bring oxygen and nutrients to the damaged tissues, and a flow of lymph is needed to carry away waste products. Physical therapy is indicated when such flows are inadequate.

For animal therapy, it is customary to apply heat to the affected area. This brings a supply of blood to the area but does nothing to carry away waste products. Alternatively, massage induces circulation, but it does nothing for deep-seated injuries.

The veins have a one-way valve action favoring only a return flow of blood, i.e., back from the extremities of the body. Thus any squeezing or stretching action of the veins will move blood and lymph toward the heart, so that fresh blood can be more available, for pumping through the arteries by the heart, to oxygenate and feed the muscles. This is a part of nature's healing process, and it is this process which the invention aids through muscle stimulation.

It is an object of the invention to provide an improved device of the character indicated.

Another object of the invention is to provide such a device for particular use in equine electrotherapy.

A further object is to provide such a device with signal-generator equipment that includes in one package, preferably portable, all safety measures, to the end that body-connection and applicator electrodes can be rugged, simple and essentially foolproof, with maximum safety to both the therapist and the equine or other living body to which the electrodes are applied.

It is also an object to meet the above objects with improved electrotherapy apparatus which may utilize relatively high voltages in application to a living body and which may, nevertheless, be applied with complete safety to human or animal bodies, more or less regardless of the area of contact with skin or hide, more or less regardless of the hair density at the locale of application, and also more or less regardless of the sweat condition of the skin or hide.

Other objects and various further features of novelty and invention will be pointed out or will occur to those skilled in the art from a reading of the following specification in conjunction with the accompanying drawings. In said drawings, which show, for illustrative purposes only, a preferred form of the invention:

FIG. 1 is a simplified view in perspective showing a stimulator of the invention;

FIG. 2 is an electrical circuit diagram, schematically showing components of the stimulator of FIG. 1;

FIG. 3 is an enlarged longitudinal sectional view of a circuit element, fixed to and part of the output circuit of the stimulator of FIG. 1;

FIG. 4 is a simplified view in perspective of a body-grounding means used with the stimulator of FIG. 1;

FIG. 5 is a view in side elevation, partly broken-away and in section, to show one body-applicator electrode for use with the stimulator of FIG. 1;

FIGS. 6 and 7 are simplified views in perspective to show other body-applicator electrodes; and FIGS. 8 to 10 are simplified diagrams to illustrate use of the electrodes of FIGS. 4 to 7.

The stimulator of FIG. 1 is seen to comprise a housing 10 which is of sufficiently light weight and size as to be portable by means of a shoulder strap 11. The stimulator is self-contained, with its own battery and electronic circuitry, to be described in connection with FIG. 2. At the front longitudinal end, a panel 12 includes a battery-charging jack 13, an on-off switch 14 and indicator lamp 15, a pulse-rate selection switch 16, an adjustment knob 17 for intensity control, and an output jack 18 for removable plug connection to the flexible insulated cable 19 of a ground or return electrode assembly. Also accessible via the front end is an output jack 20 for removable plug connection to the flexible insulated cable 21 of a body-applicator electrode assembly. The output jack 20 is at the exposed end of a coupling device 22 contained in a protective case 23, secured to and forming part of the housing 10; the coupling device 22 will be later described, in connection with FIG. 3.

The stimulator of FIG. 1 produces across the output jacks 18-20 a regular succession of pulsed wavetrains wherein the steep wall at initiation of each such wavetrain is believed to be primarily responsible for important therapeutic effects upon a body with which the electrodes of cables 19-21 are serially connected. And for equine electrotherapy, it has been found that selective availability of two pulse rates provides adequate coverage of the range of body conditions to be treated. Thus, the switch 16 has two positions, to serve the respective available pulse rates. Both pulse rates are below the rate which would induce a tetanic-contraction response, and I have found it satisfactory to provide at 16 selective availability of a "slow" rate of 4 or 5 pulses per second and a "fast" rate of 11.5 pulses per second, i.e., approaching but short of a tetanic-contraction rate. Reference to such rates will be understood to mean that they apply to the periodicity with which successive initial steep-walled pulses are delivered to the body via cables 19-21. For a given intensity setting, the slower rate is more stimulating than the faster.

The circuit within housing 10 is schematically shown in FIG. 2, wherein the externally available controls and connections are given the same identification numbers as in FIG. 1. A battery 25, as of the nickel-cadmium variety, is serially connected via switch 14 and intensity control 17 to a solid-state power supply 26. The a-c output of power supply 26 is transformer-coupled to full-wave rectifier means 27 which produces charging voltage to a capacitor 28. A trigger 29 periodically discharges capacitor 28 through an output step-up transformer 30; peak voltage across the transformer secondary may run in thousands, depending upon the control-setting at 17. The "return"-jack end 18 of the transformer secondary is grounded, and the other end is series-connected via coupling means 22 to the applicator jack 20. A "return" electrode 31 and body-applicator electrode 32 are shown connected to jacks 18-20.

The trigger 29 is activated by the uniformly spaced pulse output of oscillator and generator means 33. Pulse spacing is uniform by reason of operation from the constant-voltage output of regulating means 34, and pulse rate is a function of the time constant attributable to circuit-insertion of one or the other of two resistors 35-36, in accordance with selection by means 16; and if requisite voltage cannot be produced by regulator 34, the indicator light 15 is automatically extinguished.

It should be explained that the exact mechanism by which my machine achieves its results is not fully understood. However, certain relationships are believed to be significant and should be noted. For the electrotherapy involved in discrete neuromuscular excitation for each applied pulse, i.e., non-tetanic excitation as contemplated by either of the rate selections available at 16, it is preferred that the initial steep-walled rise of each pulse train shall be of positive polarity at the applicator output jack 20, with respect to that at the "return" jack 18. Since the useful part of the body-applicator pulse is thus positive, I have applied the positive symbol (+) at 20, and the jack 18 is marked (−) to suggest the relatively negative polarity of the "return" path, so far as pulse usefulness is believed to exist. This explanation is necessary because if the "return" jack 18 is always grounded, as shown, it certainly cannot be negative in the conventional sense of negative with respect to ground. Furthermore, since the coupling means 22 is incapable of d-c conduction, the wave-train swings must be symmetrical about the ground-neutral axis, when considered for the full length of each wavetrain. Thus, the positive (+) and negative (−) labeling and textual references herein will be understood to apply to relative polarity in relation to the initial and useful steep-walled portion of each of the successive applied pulses.

A further word of explanation will also be helpful in regard to the relative size of the electrodes 31-32, which may take various forms, as will appear from later discussion. In general, the "return" electrode 31 is in all cases relatively large, i.e., it presents a relatively large-area effective coupling to the body, with resulting relatively low-density flux at body coupling. On the other hand, the body-applicator electrode 32 is relatively small in terms of its ability to establish area coupling to the body, and therefore relatively high-density flux is characteristic of body-applicator coupling to the body. This of course means that treatment via the relatively greater flux density at the body-applicator electrode can be effectively localized to the muscles or muscle groups served by the nerves via which such local coupling is established, by selectively placed application of electrode 32 to the body.

Turning now to FIG. 3, the coupling device 22 will be seen to comprise an elongate envelope 40 of high-strength dielectric material such as glass. Envelope 40 is closed at its ends and sealed with a filling of an inert gas such as argon. A tubular electrode 41 is fixedly supported within and at one end of envelope 40, with electric-lead connection through the glass to a cable 42 for coupling to the ungrounded end of transformer 30, as at the jack-and-plug connection suggested at 43 in FIG. 2.

The envelope 40 is contained within a rigid outer tube 44 of insulating material, extending in full longitudinal overlap with and containment of envelope 40. Rigid support by and spacing within tube 44 are provided at the electrode end, using a tubular bushing 45 of insulating material, suitably counterbored to accept mounting insertion of the electrode end of envelope 40, and with supporting envelope overlap extending to substantially the longitudinally central region, as shown. At entrance of cable 42, a plug or potting 46 assures a sealed integrity of the parts 42-44-45. At its other end 47, bushing 45 is reduced and threaded, to accept a nut 48 for squeezed permanent application of seal material 49, in peripherally continuous contact with envelope 40; silicone rubber provides a suitable seal at 49, being allowed to harden after squeezing by nut 48.

The other end of envelope 40 thus projects in radially spaced relation within the remainder of tube 44. At its outer end, tube 44 is characterized by a counterbore 50, for removable telescoping reception of a cup-shaped element 51 by which jack 20 is electrostatically coupled to the conductive gas in envelope 40. As shown, element 51 has an outer skirt which is spaced from envelope 40 and is lined at 52 with moisture-retaining material such as viscose sponge. An electrically conductive mat 53, such as a tubular length of copper-screen material, is secured between the absorbent lining 52 and the skirt wall of element 51, and mat 53 has a conductive connection 54 to jack 20, at the closed end of element 51. For use, the lining 52 is wetted with tap water, causing such swelling and softening as to assure gentle but longitudinally and circumferentially continuous interference fit and form-fitting contour adaptation to the sponge-overlapped end part of envelope 40, the limit of insertion being determined by the inner end of counterbore 50. The sealed relation of the parts thus assembled is such that the wetted sponge will retain its moisture for prolonged periods of applicator use.

For dimensional illustration in the present context, a satisfactory coupling device 22 comprises a glass envelope 40 of five-eighth inch outer diameter, containing an electrode 41 which is a thin metal tube with a conically tapered end 41′, presenting a sharply defined reduced circular discharge edge of approximately three-sixteenth inch diameter. The argon-gas filling is to approximately atmospheric pressure. The length X of sponge 52 overlap with envelope 40 may be as small as one inch but is preferably two inches, and the longitudinal spacing Y between electrode 41 and sponge 52 is at least two inches and preferably about three inches.

In the equine electrotherapy for which I have indicated my stimulator to be well adapted, I have employed a surcingle 60 as the means of supporting an arcuate flexible return-electrode plate 61 (FIG. 4), having flexible-cable means 19 for connection to the stimulator circuit at jack 18. The surcingle 60 is shown as a belt of canvas, the same being relatively wide so that inner loops 62 may receive and laterally stabilize the plate 61; it will be understood that although the expression "plate" has been used as part 61, the function of this part may be served equally by a metal plate or by an electrically conductive woven insert, being in either case electrically conductively united to cable 19. The arcuate extent of plate 61 is preferably sufficient to enable conformation to an extensive span of the animal's back approaching one half the body girth, and the reduced ends of the canvas body of the surcingle may be sewn with buckle-fitted webbing straps 63, for secure application to the body, as shown in the diagrams of FIGS. 8 to 10. In application to the body, a wetted towel (e.g., 64, in FIG. 8) is first laid over the animal's back, for interposition between plate 61 and the body, thus assuring large-area and low-density distribution of the "return" flux.

For motional sweep of a muscle group to be treated, I have obtained highly satisfactory results with a body applicator of the type shown in FIG. 5, and resembling a paint roller. This applicator is shown to comprise an insulating handle 65 with insulating-cable connection 21 to a conductive bent-rod frame which establishes a straight outer transverse span 66 for roller support; a jacket 67 of insulating material covers this bent rod between handle 65 and the roller-supporting span 66. The roller itself may comprise a rigid tube 68, as of phenolic-impregnated carboard. Conductive means such as plural angularly spaced elongate copper wires 69 are bonded to the outer surface of tube 68; their ends extend beyond the ends of tube 68 and are bent around the tube ends and into adjacent end regions of the bore of the tube, for secure electrical contact with supporting flange formations of metal end-bell members 70 which are free to rotate on the rod span 66. A washer 71 is interposed between the right-end member 70 and a locating plug 72 struck up from rod material 66; and lock nuts 73 at the threaded outer end of span 66 assure integrity of the assembly via both the opposed end-bell members 70. A circumferential layer 74 of moisture-absorbent material such as viscose sponge is bonded to the outer periphery of tube 68 for moistened conductive relation to cable 21 via conductors 69, end-bell members 70, and rod 66, as will be understood.

FIG. 6 illustrates another one of my body-applicator electrodes, useful in equine electrotherapy, particularly when the area of application is to be very localized. The applicator is merely a conductive knob 75, with electrical connection to an insulated connection cable 21', and with an insulating handle or grip portion 76. Applicator 75 is used dry, over wet or dry skin.

FIG. 7 illustrates a further body-applicator electrode, particularly useful when a particular leg section is to be given a more sustained exposure to electrotherapy. The applicator of FIG. 7 comprises a short collar or arcuate plate 80 of flexible metal (or conductive fabric), to the outer surface of which a blanket 81 of insulation and a covering 82 of canvas has been laminated. Buckle-fitted straps, as at 83, are sewn to the covering 82, for selective connection at 84. An externally accessible electrical terminal 85 to plate 80 is shown with alligator spring-clip connection to an insulated cable 21". In use, a wetted viscose sponge is applied between the animal's leg and plate 80, before fastening at 84.

FIGS. 8, 9 and 10 respectively illustrate use of the applicators 32 (FIG. 5), 75 (FIG. 6), and 80 (FIG. 7) to the body of the animal, with ground or return electrode coupling via the surcingle of FIG. 4.

In equine use, the return assembly is first fitted on the animal, in the manner already described, placing a wet towel or the like between the plate 61 and the back region indicated. An appropriate body-applicator electrode is then selected, the knob (FIG. 6) or roller (FIG. 5) being for application to heavily muscled areas, the strap-on (FIG. 7) or roller (FIG. 5) being usable for lower-leg treatment. The coupling lining 52 should be wet and fully inserted at 50. The instrument (FIG. 1) may then be slung from the operator's shoulder, under either arm, and with the panel controls conveniently accessible; the power switch 14 should be off, and the intensity control 17 should be at its lowest setting, before cable-plug connections for the electrodes are made to the jacks 18-20. The power switch may then be turned on, but intensity control at 17 should be kept low until the body-applicator electrode is in animal contact at the treatment area.

To begin treatment, the applicator should be moved slowly over the treatment area as intensity is gradually increased, by adjustment at 17. As the moving applicator passes nerve motor points, muscles will respond in the areas served by these motor points by contracting in cadence with the pulse rate selected at 16. It is not necessary to produce spectacular muscle action to achieve desired results; the intensity setting should always be at a comfortable level, which may vary considerably between individual horses and between different areas on the same horse. And pressure on the applicator should be firm, particularly with the knob type (FIG. 6) because it is of such reduced effective area and is intended to be used dry, i.e., without a wet-sponge intermediary.

The best technique is to move the applicator around the treatment area, stopping briefly over each motor point. The roller (FIG. 5) moves easily back and forth, and the knob (FIG. 6) can be applied in a circular massaging motion. From the animal's reactions, the therapist can judge the treatment time for each case. Generally, the motor points can be beneficially stimulated in a pattern of intermittent coverage, allowing five to ten contractions before moving to another spot, and then returning to the same motor point; this procedure should be repeated in the treatment area for a total of ten or twenty minutes. When using the strap-on applicator (FIG. 7), stimulation should be given for three to five minutes, turned off for one minute, and then repeated in this manner for a total of about twenty minutes.

In all cases, the intensity control 17 should be reduced to the full-low setting, before discontinuing treatment and before removing the applicator from the animal. If intensity is high and the applicator is in close but not good body contact, a static spark may be drawn between the applicator and the animal. This is harmless but might startle the therapist or the animal.

The described stimulator will be seen to have achieved all stated objects; however, it is not represented as a cure-all, for application to any ailment or injury. The electrical discharge or transient current has not known beneficial effect per se, but its proper use does increase circulation indirectly by inducing muscle activity. The stimulator of the invention does this in a manner which can be readily tolerated by horses and other animals and humans. In general, equine use of the stimulator is indicated in the following situations:

1. General muscle soreness.
2. Bruised muscles.
3. Tying-up of back muscles.
4. Swelling and filing of joints and lower legs.
5. For relaxation of muscles prone to tightness.

But use of the stimulator is contra-indicated in situations where:

1. There may be a danger of hemorrhage, as with the case of an open wound or freshly bowed tendons.
2. Treatment calls for reducing circulation, to localize certain types of infection.
3. A skeletal injury could be aggravated by muscle action in the immediate vicinity. However, beneficial circulation can be induced by stimulation of muscles close to the area of injury.

While the invention has been described in detail for a particular embodiment, it will be understood that modifications may be made without departing from the invention.

What is claimed is:

1. In an electrophysical neuromuscular stimulator of the character indicated, a frame, pulse-generator means carried by said frame and including a ground connection and an output line developing with respect to said ground connection a train of voltage pulses having polarized steep-walled wavefronts, selectively operable means for varying the pulse-repetition rate to enable selection of a rate insufficient to produce tetanic contraction, manually operable means for selectively controlling the amplitude of said voltage pulses, said output line including a sealed elongate tubular dielectric envelope containing a conductive gas and mounted to said frame, an electrode within said envelope at one end thereof and having a conductive connection through said end of said envelope and forming part of said output line, and an output body-electrode coupling connection including a conductive tubular portion having a bore removably assembled in telescoping longitudinal overlap with the other end of said envelope, said conductive tubular portion being longitudinally offset from said electrode, the envelope mounting to said frame comprising body means of insulating material rigidly positioning the electrode end of said envelope and including a tubular shroud overlapping at least the remainder of said envelope and in radial clearance therewith, said coupling connection being supported by said shroud, and radially compliant moisture-absorbent means in circumferential and longitudinal contact with said other end of said envelope and in circumferential and longitudinal contact with the bore of said conductive tubular portion.

2. In an electrophysical neuromuscular stimulator of the character indicated, a frame, pulse-generator means carried by said frame and including a ground connection and an output line developing with respect to said ground connection a train of voltage pulses having polarized steep-walled wavefronts, selectively operable means for varying the pulse-repetition rate to enable selection of a rate insufficient to produce tetanic contraction, manually operable means for selectively controlling the amplitude of said voltage pulses, said output line including a sealed elongate tubular dielectric envelope containing a conductive gas and mounted to said frame, an electrode within said envelope at one end thereof and having a conductive connection through said end of said envelope and forming part of said output line, and an output body-electrode coupling connection including a conductive tubular portion having a radially compliant moisture-absorbent bore in circumferential and longitudinal contact with said other end of said envelope, said conductive tubular portion being removably assembled in telescoping longitudinal overlap with said other end of said envelope, and said conductive tubular portion being longitudinally offset from said electrode.

3. The stimulator of claim 2, in which the envelope mounting to said frame comprises an elongate tube of insulating material of greater longitudinal extent than said envelope and fixedly supporting the electrode end of said envelope within and near one end of said insulating tube, the remainder of said insulating tube overlapping at least the remaining length of said envelope and in radial clearance therewith, said coupling connection being supported by said insulating tube with said tubular portion in telescoping overlap with said insulating tube and within said clearance.

4. The stimulator of claim 2, in which said envelope is mounted to and externally of said frame, and an auxiliary protective housing containing said envelope and secured to a side wall of said frame.

5. As an article of manufacture, an output-circuit element for fixed mounting to the frame of an electrophysical neuromuscular stimulator of the character indicated, said circuit element comprising a sealed elongate tubular dielectric envelope containing a conductive gas and adapted for mounting to said frame, an electrode within said envelope at one end thereof and having an external conductive connection through said end of said envelope and adapted to form one terminal part of the series-connection of said element in an output-circuit line, and an output body-electrode coupling connection including tubular radially compliant moisture-absorbent means having a bore removably assembled in telescoping circumferential and longitudinal contacting overlap with the other end of said envelope, said coupling connection including a conductive member extending to and contacting said moisture-absorbent means and being adapted to form a second terminal part of the series-connection of said element in the output-circuit line, said telescoping overlap being at longitudinal offset from said electrode.

6. The article of claim 5, in which an elongate tube of insulating material is adapted for such fixed frame mounting, said insulating tube being of greater longitudinal extent than said envelope and fixedly supporting the electrode end of said envelope within and near one end of said insulating tube, the remainder of said insulating tube overlapping the remaining length of said envelope and in radial clearance therewith.

7. The article of claim 6, in which said insulating tube has a counterbore at the coupling-connection end, said counterbore having an axial depth determining the extent of said telescoping overlap, and in which said coupling connection includes a cupped rigid body of insulating material with an external skirt profile supported in the counter bore, the conductive member of said coupling connection extending through the closed end of said cupped body.

8. The article of claim 5, in which said electrode includes a gas-exposed elongate cylindrical outer surface in radial clearance within the adjacent inner surface of said envelope.

9. The article of claim 8, in which the gas-exposed surface of said electrode is of substantially greater axial than radial extent.

10. The article of claim 8, in which the gas-exposed surface of said electrode is of substantially greater axial extent than the bore diameter of the adjacent end portion of said envelope.

11. The article of claim 8, in which the axial extent of said telescoping overlap is in the order of magnitude of the gas-exposed axial extent of said electrode.

12. The article of claim 5, including a surrounding and supporting rigid outer tubular member fixedly supporting the electrode end of said envelope, the extent of fixed support of the electrode end of said envelope being longitudinally past overlap with said electrode and into axial proximity with said coupling connection.

13. The article of claim 12, in which seal means including a plug of insulating material seals said envelope to the bore of said outer tubular member at the region of supported axial proximity with said coupling connection.

14. The article of claim 12, in which said coupling connection includes a cupped body of insulating material fitted in the end of the bore of said outer tubular member in axial proximity with said coupling connection, the conductive member of said coupling connection extending through the closed end of said cupped body.

* * * * *